United States Patent
D'Onofrio et al.

(10) Patent No.: US 11,717,653 B2
(45) Date of Patent: Aug. 8, 2023

(54) DRUG-COATED ANGIOPLASTY BALLOONS

(71) Applicant: Medtronic Vascular, Inc., Santa Rosa, CA (US)

(72) Inventors: Simone D'Onofrio, Coccaglio (IT); Massimo Morero, Bricherasio (IT); Federica Bellucci, Alessandria (IT); Bradley E. Steele, Plymouth, MN (US); Diane M. Haen, St. Louis Park, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 450 days.

(21) Appl. No.: 16/887,307

(22) Filed: May 29, 2020

(65) Prior Publication Data

US 2021/0370028 A1 Dec. 2, 2021

(51) Int. Cl.
- *A61M 25/10* (2013.01)
- *A61K 31/436* (2006.01)
- *A61L 29/08* (2006.01)
- *A61L 29/16* (2006.01)

(52) U.S. Cl.
CPC ......... *A61M 25/104* (2013.01); *A61K 31/436* (2013.01); *A61L 29/085* (2013.01); *A61L 29/16* (2013.01); *A61M 25/1029* (2013.01); *A61L 2300/204* (2013.01); *A61L 2300/21* (2013.01); *A61L 2300/216* (2013.01); *A61L 2300/416* (2013.01); *A61L 2300/63* (2013.01); *A61L 2300/802* (2013.01); *A61L 2420/02* (2013.01); *A61M 2025/105* (2013.01); *A61M 2025/1031* (2013.01)

(58) Field of Classification Search
None
See application file for complete search history.

(56) References Cited

U.S. PATENT DOCUMENTS

| | | | |
|---|---|---|---|
| 8,257,305 | B2 | 9/2012 | Speck et al. |
| 8,608,689 | B2 | 12/2013 | Scheller et al. |
| 9,539,369 | B2 | 1/2017 | Peters |
| 2012/0303115 | A1 | 11/2012 | Dadino et al. |
| 2013/0053947 | A1* | 2/2013 | Kangas ............... A61K 31/436 623/1.42 |
| 2016/0228617 | A1* | 8/2016 | Peters ............... A61M 25/104 |
| 2020/0038560 | A1 | 2/2020 | Cerchiari et al. |
| 2020/0171281 | A1* | 6/2020 | D'Onofrio ........... A61K 31/573 |

FOREIGN PATENT DOCUMENTS

| | | |
|---|---|---|
| EP | 2550030 | 1/2013 |
| EP | 3603688 | * 7/2019 |

OTHER PUBLICATIONS

U.S. Appl. No. 16/696,846, filed Nov. 26, 2019, D'Onofrio et al.
Partial European Search Report from EP Application No. 21176193.7 dated Oct. 8, 2021, 15 pages.
Extended European Search Report from EP Application No. 21176193.7 dated Jan. 27, 2022, 14 pages.

* cited by examiner

*Primary Examiner* — Danah Al-Awadi
(74) *Attorney, Agent, or Firm* — Mueting Raasch Group

(57) ABSTRACT

Angioplasty balloons coated with at least one limus drug, which may be in crystalline form, optionally with at least one excipient, and methods for manufacturing such coated angioplasty balloons.

20 Claims, 3 Drawing Sheets

DRUG-COATED ANGIOPLASTY BALLOONS

FIELD

The present disclosure relates to angioplasty balloons coated with a drug, and to methods for manufacturing such coated angioplasty balloons.

BACKGROUND

An "angioplasty balloon," also referred to as a "dilation balloon," "catheter balloon," or "balloon catheter" denotes angioplasty balloon catheters that are used to treat coronary and peripheral artery disease. In one common application, a balloon catheter is used in a percutaneous transluminal coronary angioplasty (PTCA) procedure. In a PTCA procedure, the balloon catheter is threaded through an artery to a site of a lesion. The balloon is inflated to compress plaque associated with coronary artery disease against the artery's walls. This creates a larger opening in the artery and helps restore adequate blood flow. The balloon is then deflated and withdrawn from the vessel.

Balloon catheters are also used in combination with stents to treat coronary disease. A stent is a miniature mesh tube, typically made from steel. The balloon catheter and stent are threaded through an artery to the site of a lesion. The balloon is inflated to expand the stent. The stent is flexible, yet strong enough to remain in place after the balloon is deflated and cleared. Once the stent is in place, the balloon is deflated and withdrawn from the vessel.

Such angioplasty balloons coated with drugs have been described or used for many years. The drugs may be used alone or with excipients or polymers. In some instances, a polymer is employed to control the release rate. In some instances, the bare drug is coated on the device to facilitate rapid release and bioavailability.

Rapid release may be desirable in situations where time of contact between the device and the tissue to which the drug is delivered is minimal. For example, catheter balloons used for angioplasty procedures (i.e., angioplasty balloons) are often contacted with vascular tissue for short durations, and, thus, antiproliferative agents coated on the balloons for treating or preventing restenosis should be rapidly released from the balloon and transferred to the vascular tissue.

However, the effect of the transferred antiproliferative drugs should last for weeks or months because such a time frame may be important for preventing restenosis. Preferably, the antiproliferative drug is in a form that may remain active at the treated tissue for extended periods of time. Different crystalline or amorphous forms of drugs may differ in sustained availability. For example, amorphous forms of drugs tend to be more rapidly released and more immediately bioavailability, relative to crystalline forms, but tend to have a less sustained therapeutic effect. Thus, a drug-coated angioplasty balloon that has a balance between release rate, bioavailability, and sustained therapeutic effect is still needed.

SUMMARY

The present disclosure describes, among other things, angioplasty balloons coated with a limus drug and to methods for manufacturing such coated angioplasty balloons.

In some embodiments, the present disclosure describes an angioplasty balloon comprising a surface having disposed thereon a single-layer coating comprising at least one limus drug, a portion of which is in the form of crystals, wherein no more than 30 wt-% of the total limus drug is in the form of crystals, and further wherein the angioplasty balloon is in a deployable configuration.

In some embodiments, the present disclosure describes an angioplasty balloon comprising a surface having disposed thereon a single-layer coating comprising at least one non-polymeric excipient and at least one limus drug (in some embodiments, a portion of the limus drug is in the form of crystals), wherein the excipient is present in the single-layer coating in a limus drug to excipient ratio of greater than 20:1, and further wherein the angioplasty balloon is in a deployable configuration.

In some embodiments, the present disclosure describes a method of coating an angioplasty balloon, the method comprising: forming a coating solution comprising at least one limus drug and a mixture of organic solvents, at least two of which have different rates of evaporation; applying the coating solution to a surface of an angioplasty balloon in one step using needle deposition; and allowing the mixture of solvents to evaporate and form a single-layer coating comprising at least one limus drug (in some embodiments, a portion of the limus drug is in the form of crystals). In certain embodiments, the method further includes forming the coated angioplasty balloon into a deployable configuration.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

In this disclosure, terms such as "a," "an," and "the" are not intended to refer to only a singular entity but include the general class of which a specific example may be used for illustration. The terms "a," "an," and "the" are used interchangeably with the term "at least one."

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise. The term "and/or" means one or all of the listed elements or a combination of any two or more of the listed elements.

Also herein, unless otherwise specified, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used.

Also herein, the recitations of numerical ranges by endpoints include all numbers subsumed within that range as well as the endpoints (e.g., 1 to 5 includes 1, 1.5, 2, 2.75, 3, 3.80, 4, 5, etc.). Herein, "up to" a number (e.g., up to 50) includes the number (e.g., 50).

The term "in the range" or "within a range" (and similar statements) includes the endpoints of the stated range.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure.

Furthermore, the particular features, configurations, compositions, or characteristics described herein may be combined in any suitable manner in one or more embodiments. That is, any one of the features of the embodiments, examples, or aspects described herein may be combined with any other feature of another embodiment, example, or aspect described herein.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list. Thus, the scope of the present disclosure should not be limited to the specific illustrative structures described herein, but rather extends at least to the structures described by the language of the claims, and the equivalents of those structures. Any of the elements that are positively recited in this specification as alternatives may be explicitly included in the claims or excluded from the claims, in any combination as desired. Although various theories and possible mechanisms may have been discussed herein, in no event should such discussions serve to limit the claimable subject matter.

The schematic drawings presented herein are not necessarily to scale.

DETAILED DESCRIPTION

This disclosure relates to, among other things, angioplasty balloons coated with at least one limus drug, which may be in crystalline form, optionally with at least one excipient, and to methods for manufacturing such coated angioplasty balloons.

The limus drug-containing coating is in the form of one layer. Thus, for example, if the coating includes a limus drug and an excipient, they are combined in a mixture within one layer. By single layer, it is meant that there is no overlayer or overcoating with a secondary drug and/or excipient.

In certain embodiments, the excipient is nonpolymeric (i.e., it is a low molecular weight small molecule). In certain embodiments, the drug-containing coating is a polymer-free coating so that the limus drug may be rapidly released from the balloon when the balloon contacts the target tissue.

The limus drug-containing coating adheres well to the balloon surface with little or no loss due to handling, tracking through vasculature, and shear stress caused by blood flow. The coating transfers a therapeutic amount of the limus drug from the balloon surface to the vessel wall during balloon inflation. Ideally, the transferred drug provides desirable bioavailability, particularly long-term bioavailability (e.g., even over periods of time as long as 30-180 days).

In some embodiments, the limus drug is immediately released and bioavailable at the site of intervention. As used herein, "site of intervention" means the section of the blood vessel treated directly with an angioplasty balloon, and the adjacent portion in the tissues of which the post-procedure presence of the drug can be detected. Generally, such section will extend for 2 millimeters (mm) to 10 mm down- and up-stream of the contact section with the balloon. As used herein, "an immediate release and bioavailabile" means a release from the angioplasty balloon surface in periods of time, for example, ranging from 1 second to 1.5 minutes, preferably from 20 seconds to 1 minute, and an absorption by the tissue in periods of time, for example, ranging from 1 second to 25 minutes, preferably from 20 seconds to 25 minutes.

Figure 1:
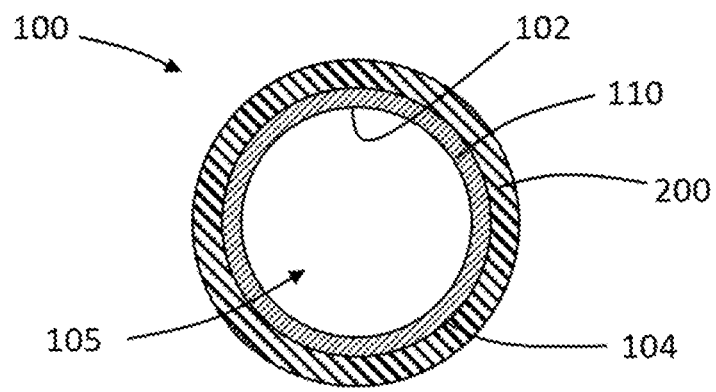
FIG. 1 is a schematic sectional view of an embodiment of an angioplasty balloon having a coating as described herein disposed thereon.

Referring now to FIG. 1, a cross-sectional view of an inflated angioplasty balloon 100 is shown. The angioplasty balloon 100 comprises a body or wall 110 defining an interior surface 102 and an exterior surface 104, the interior surface 104 defining an interior space 105. A single layer 200 comprising a limus drug, a portion of which is crystalline, and optional an excipient mixed with the limus drug, is disposed on the exterior surface 104 of the angioplasty balloon 100.

In the context of the present disclosure, the angioplasty balloon is in a deployable (i.e., collapsed) configuration. A deployable configuration is one in which the balloon is configured to have a low profile for travel along a relatively long pathway within the healthy blood vessels, while being exposed to the blood stream (i.e., ready for treatment). A wide variety of deployable (i.e., collapsed) configurations can be envisioned; typically, however, balloons in such a configuration may be pleated, folded, or both.

In one example, a dilatation catheter includes an elongate flexible shaft having a dilatation balloon carried at the distal end of the shaft. An inflation lumen extends through shaft from the proximal to the distal end and is in fluid communication with the interior of balloon. The balloon is a tubular polymeric member formed to collapse under the influence of reduced internal pressure into a configuration defined by at least three longitudinally extending wings characterized in that the tubular body has a segment of reduced thickness between adjacent wings to provide a folding pleat whereby the tubular body defines at least three longitudinally extending pleats and alternating wings. The segments are lines extending longitudinally of the tubular body.

In another example, a balloon includes (in the collapsed configuration) a plurality of folds that are laid in a tangential (or circumferential winding) direction about the balloon, wherein the folds originate from distinct longitudinal lines along the outer wall of the balloon and are arranged in pairs, and wherein the folds are wrapped in such a way that a fold of one pair overlaps an adjacent fold of another pair.

In yet another example, a balloon assembly includes an inner member and a balloon mounted thereon and folded in an accordion manner. The balloon includes a plurality of pleats on either side of the inner member. The balloon can have an equal number of pleats on either side of the first inner member, or can be folded in an asymmetrical manner. The balloon can also be folded in a tri-fold accordion manner.

Figure 2:
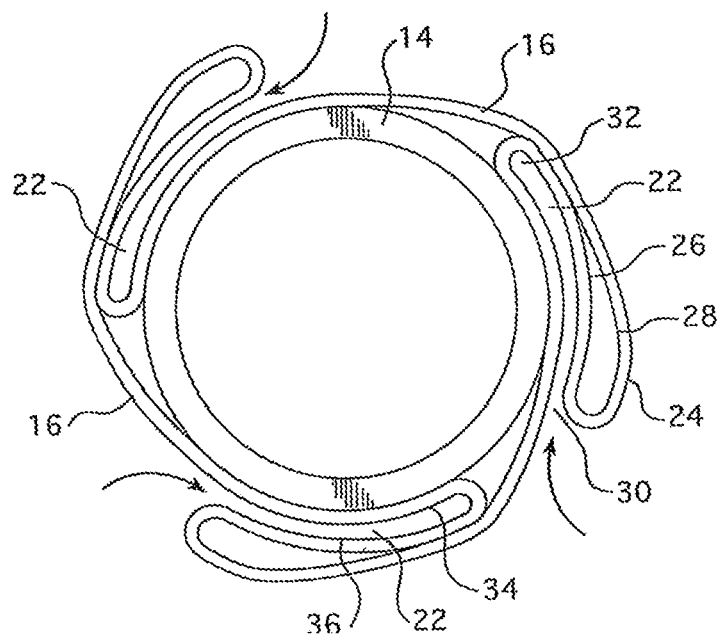
FIG. 2 is a schematic of an embodiment of a folded and pleated angioplasty balloon.

An exemplary angioplasty balloon as shown in FIG. 2 includes a folded balloon 16 that consists of pleats 24 that are pressed together and then wrapped substantially uniformly around the inner shaft 14 of the balloon catheter. A closed space is formed by the inner surface 26 of the pleat 24 to the outside surface 28 and the portion of the balloon 16 adjacent to the inner shaft 14. The fold 22 is characterized by a depth defined as the distance from the entrance 30 to the fold 22 to its bottom 32, a width defined as the distance from the inside surface 34 of the fold 22 to its outside surface 36, and a length defined as the axial distance from the most distal point of the fold 22 to its most proximal point.

Any of these configurations, or more, may be used with the angioplasty balloons described herein coated with at least one limus drug, which may be in crystalline form, optionally with at least one excipient.

Angioplasty Balloons

An "angioplasty balloon," also referred to as a "dilation balloon," "catheter balloon," or "balloon catheter" denotes angioplasty balloon catheters, i.e., balloon catheters for percutaneous transluminal angioplasty to dilate or reopen stenosed or occluded blood vessels (usually arteries, less frequently also veins) by means of balloon dilatation. Coatings for angioplasty balloons adhere to the balloon en route to the stenosed and/or occluded segment of the blood vessel, i.e., while the balloon is being guided through a hemostatic valve, as well as on the path through an insertion loop filled with blood and/or through a guide catheter and through proximal portions of the blood vessel and then must dispense the active ingredient to the vascular wall rapidly, while the balloon is being filled. After the operation, the angioplasty balloon does not remain in the body, in contrast with an implant such as a stent or an implantable or indwelling catheter.

The balloon material may be compliant, semi-compliant, or non-compliant. The balloons may be formed from any suitable material. For example, the balloons may be formed of a polyamide, polyethylene terephthalate (PET), polyurethane, latex, silicone, polyethylene (PE), polypropylene (PP), polyetherimide (PEI), polytetrafluoroethylene (PTFE), ethylene tetrafluoroethylene (ETFE), fluorinated ethylene propylene (FEP), polyoxymethylene (POM), polybutylene terephthalate (PBT), polyether-block-ester, polyvinylchloride (PVC), polyether-block-amide (PEBA), polyetheretherketone (PEEK), polyimide (PI), polyphenylene sulfide (PPS), polyphenylene oxide (PPO), poly(ethylene naphthalenedicarboxylate) (PEN), polysulfone, perfluoro(propyl vinyl ether) (PFA), or mixtures, combinations, copolymers thereof, and the like. In some embodiments, the balloon is made of nylon 12.

Limus Drugs

The limus drugs are anti-restenosis agents selected from sirolimus (i.e., rapamycin), everolimus, zotarolimus, biolimus, temsirolimus, myolimus, novolimus, ridaforolimus, tacrolimus, and pimecrolimus. In certain embodiments, sirolimus and zotarolimus are preferred. In certain embodiments, sirolimus is preferred, particularly in embodiments in which a portion of the limus drug is in crystalline form. "At least one limus drug" means that mixtures of several limus drugs may be used; however, a single limus drug is preferably used.

The drug on the surface of the balloon may be in a crystalline form, an amorphous form, or a combination of crystalline and amorphous forms. In certain preferred embodiments, the limus drug is in crystalline form. For example, in some embodiments, the present disclosure describes an angioplasty balloon comprising a surface having disposed thereon a coating comprising at least one limus drug, a portion of which is in the form of crystals. In certain embodiments, at least 1 wt-% of the total limus drug is in the form of crystals. In certain embodiments, no more than 30 wt-%, no more than 25 wt-%, or no more than 20 wt-%, of the total limus drug is in the form of crystals. Generally, the greater the amount of crystalline form of the limus drug, the greater the sustained bioavailability of the drug in the tissue of the patient; however, the crystalline form also slows down the drug's release from solid state to free/solubilized state. The drug is only therapeutic when it is solubilized. Thus, the balance of crystalline vs amorphous forms impacts the amount of free drug available to tissue.

The presence and amount of crystalline limus drug can be determined by X-ray diffraction (XRD). For example, the main XRD peaks of crystalline sirolimus include: high intensity peaks (7°, 10°, and 15°); and low intensity peaks (5°, 11°, 13°, and several peaks in the 20-25° range).

The drug may be in one or more different polymorphs. Polymorphs may have different solubilities or crystal forms. Polymorphs may have characteristics that affect tissue uptake of the drug at the delivery site or dissolution rate in bodily fluids.

Unless content clearly dictates otherwise, general reference to a drug in the present disclosure includes reference to salts of the drug, hydrates of the drug, polymorphs of the drug, isomers of the drug (including constitutional isomers and stereoisomers such as enantiomers and diasteriomers), and the like.

The single-layer limus drug-containing coating may include drug particles having any suitable size profile. Preferably, the particulate size profile facilitates uptake by the tissue. Very small particles, such as particles less than 1 μm in size, may be taken up directly into arterial tissue. In some embodiments, the drug may be in a particulate form that has a particle size in a range from 0.01 micrometer (μm) to 20.0 μm. Different size ranges may be used in some cases to provide a desired bioavailability profile over time. For example, smaller crystals will more readily dissolve and enter the tissue for immediate effect, while larger crystals will dissolve at a slower rate enabling longer drug persistence.

One or more limus drugs is present in the single-layer coating in a therapeutically effective amount. As used herein, "therapeutically effective amount" means a drug amount capable of inducing a therapeutic or preventive effect against the disease being treated or prevented. For example, if the disease being treated or prevented is restenosis of vascular tissue, the one or more drugs present in the drug-containing coating may be present in an amount effective to treat or prevent restenosis of the treated vascular tissue in the patient.

In certain embodiments, one or more limus drugs may be present in the single-layer limus drug-containing coating at a density of at least 0.1 microgram per square millimeter ($\mu g/mm^2$), at least 0.25 $\mu g/mm^2$, at least 0.5 $\mu g/mm^2$, at least 1 $\mu g/mm^2$, or at least 3 $\mu g/mm^2$. In certain embodiments, one or more limus drugs may be present in the single-layer limus drug-containing coating at a density of up to 100 $\mu g/mm^2$, up to 50 $\mu g/mm^2$, up to 20 $\mu g/mm^2$, up to 10 $\mu g/mm^2$, up to 7 $\mu g/mm^2$, or up to 5 $\mu g/mm^2$. For example, the density may be from 0.1 $\mu g/mm^2$ to 10 $\mu g/mm^2$, or from 0.1 $\mu g/mm^2$ to 5 $\mu g/mm^2$. In some embodiments, one or more limus drugs may be present in the single-layer limus drug-containing coating at a density of from 0.25 $\mu g/mm^2$ to 20 $\mu g/mm^2$. In some embodiments, one or more limus drugs may be present in the single-layer limus drug-containing coating at a density of from 1 $\mu g/mm^2$ to 7 $\mu g/mm^2$.

Optional Excipients

In some embodiments, the present disclosure describes an angioplasty balloon comprising a surface having disposed thereon a coating comprising at least one limus drug and at least one excipient. Typically, the excipient is present to promote the release of the drug.

The excipient is preferably nonpolymeric (i.e., it is a low molecular weight small molecule). It is present in the coating in crystalline and/or amorphous form.

Suitable excipients are preferably hydrotropic agents (i.e., hydrotropes). Hydrotropes contain both hydrophobic and hydrophilic fractions in the structure. In comparison to surfactant, they contain a very small hydrophobic fraction. Hydrotropic agents can be anionic, cationic, or neutral. They can be organic or inorganic. They can be liquids or solids.

The excipients dissolve readily in aqueous solutions, as well as alcohols. Hydrotropes with an amphiphilic molecular structure possess the ability to increase the solubility of sparingly soluble organic molecules in water.

Examples of hydrotropic agents include aliphatic linear compounds including sodium alkanoate, urea, and urea derivatives (e.g., allylurea, acetamide, methyl carbamate, butyl carbamate, and N,N-dimethyl urea); aromatic anionic compounds such as sodium benzoate, sodium salicylate, sodium benzene sulfonate, sodium benzene di-sulfonate, sodium cinnamate, sodium 3-hydroxy-2-naphthoate, sodium para-toluene sulfonate, sodium cumene sulfonate, nicotinamide, N,N-diethylnicotinamide, and N,N-imethyl benzamide; aromatic cationic compounds such as para-aminobenzoic acid hydrochloride, procaine hydrochloride, and caffeine.

In certain embodiments, the excipient is urea or a urea derivative. In certain embodiments, the excipient is urea.

In certain embodiments, the excipient is present in the coating in a limus drug to excipient ratio of greater than 20:1. Higher amounts of excipient, particularly urea, are generally undesirable because they may reduce the amount of crystalline limus drug formed; however, higher amounts of excipient may provide a greater chance of long-term drug bioavailability in the tissue of a patient. Thus, a balance of limus drug to excipient is desirable to provide a balance of crystalline drug formation to bioavailability.

Method of Making

In some embodiments, the present disclosure describes a method of coating an angioplasty balloon, the method comprising: forming a coating solution comprising at least one limus drug and a mixture of organic solvents, at least two of which have different rates of evaporation; applying the coating solution to a surface of an angioplasty balloon in one step using needle deposition; and allowing the mixture of solvents to evaporate and form a single-layer coating comprising at least one limus drug, preferably including crystals.

The solvents may have any suitable degree of volatilities. For example, the solvents may have a vapor pressure of 0.0005 atmosphere or greater at 20° C. In some embodiments, the solvent has a vapor pressure of 0.03 atmosphere or greater at 20° C., such as a vapor pressure of 0.07 atmosphere or greater at 20° C., or 0.1 atmosphere or greater at 20° C. Evaporation of one of the two different organic solvents at a rate faster than the other changes the ratio of the solvents and initiates crystallization of the limus drug.

Herein, a "coating solution" does not include any visible solid material (e.g., by the unaided eye), unlike a dispersion that includes dispersed solid material (e.g., pre-formed crystals). In other words, the coating solution is preferably configured to create crystals during coating, and not pre-form crystals to be deposited on the surface of the balloon.

In certain embodiments, the mixture of organic solvents includes at least one polar organic solvent and at least one apolar organic solvent. The apolar and polar organic solvents preferably have at least a difference in their log $K_{OW}$ of 1 ($K_{OW}$=octanol/water distribution coefficient). The polar organic solvent is understood in particular to be an organic solvent having a log $K_{OW}$ between 1.0 and +2.0, preferably between 0.5 and +1.8. The apolar organic solvents are in particular understood to be organic solvents with a log $K_{OW} \geq 3$, preferably between 3 and 6.5. Polar organic solvents are also referred to synonymously and in abbreviated form as polar solvents, and the same thing is also true of the apolar organic solvents (apolar solvents).

In at least one of the solvents, preferably in the organic polar solvent, the limus drug should have a solubility of greater than 10 mg/mL, preferably greater than 30 mg/mL. The limus drug should have only a low solubility in the other solvent(s), preferably in the apolar organic solvent, for example, with less than 1 mg/mL (0.001 to 0.999 mg/mL).

Examples of volatile polar organic solvents include alcohols, acetone, ethyl acetate, and chloroform. The alcohols are understood to include monovalent or polyvalent alkanols in particular, more preferably monovalent C1-C3 alkanols, most preferably methanol, ethanol, and isopropyl alcohol. Other polar organic solvents include tetrahydrofuran, acetonitrile and diethyl ether. In certain embodiments, polar solvent includes ethyl acetate, methanol, ethanol, isopropyl alcohol, acetone, or combinations thereof.

Examples of apolar solvents include aliphatic C6-C10 hydrocarbons, for example, cyclohexane, hexane, heptane, octane, etc. In certain embodiments, the apolar solvent includes heptane, hexane, or a combination thereof.

The amount of apolar solvent is typically less than the amount of polar solvent used in a mixture of solvents. In certain embodiments, the ratio of apolar solvent to polar solvent in a coating solution is in a range of 35:65 to 45:55 (i.e., 35-45% by volume apolar solvent and 55-65% by volume polar solvent).

The mixture of solvents also includes mixtures of a plurality of solvents of one and/or both categories, but preferably one solvent is used per category. A preferred pair of polar and apolar organic solvents is, for example, ethyl acetate and heptane. The ethyl acetate evaporates faster than heptane and when the ratio of ethyl acetate to heptane reaches 1:1, crystallization of the limus drug takes place on the surface of the balloon. Another preferred pair of polar and apolar organic solvents is, for example, acetone and hexane.

In certain embodiments, only the limus drug is present in the coating solution (100% of solute is the drug). In certain embodiments, the concentration of limus drug in the coating solution is in a range of 95 wt-% to 99.9 wt-%, based on the total weight of the solute (e.g., drug and excipient) in the coating solution.

If the coating solution further includes at least one excipient, the concentration of the excipient in the coating solution is in a range of 0.1 wt-% to 5 wt-%, based on the total weight of the solute (e.g., drug and excipient) in the coating solution.

The coating solution may be formed using a variety of techniques and order of addition of components. For example, the limus drug can be dissolved in a polar organic solvent, and then the solution can be mixed with the apolar solvent, preferably to form a supersaturated solution. The excipient, particularly urea, is typically dissolved in a volatile polar organic solvent, such as an alcohol (e.g., methanol, ethanol, and isopropyl alcohol) or acetone. This is combined with a solution of the limus drug, wherein the order of addition is not critical.

Crystallization of the limus drug can be triggered by differential evaporation of the solvents after the coating solution is applied to the balloon surface (in the absence of any seed crystals). Thus, herein, "one step" means that there is no pre-application of seed crystals.

The coating solution, preferably a supersaturated solution, comprising the limus drug and optionally an excipient may be applied to an exterior surface of the angioplasty balloon using a variety of techniques known to those skilled in the art. Such techniques and process conditions may be selected to achieve crystallization directly on the balloon surface. A particularly preferred technique for applying the coating solution to ensure sufficient coating and avoid premature crystallization of the limus drug is needle deposition.

Herein, "needle deposition" involves applying the coating solution from a device through a small orifice, whether a needle is, in fact, used or not. For example, a predetermined amount of coating solution may be applied to a balloon surface using an injection device, such as, for example, a glass syringe, a pipette, a nozzle, etc., filled with the exact amount of coating solution required to achieve the desired concentration of a therapeutic on the balloon. The needle of the syringe is typically placed in close proximity to the balloon surface and the coating solution is applied to the balloon by depressing a plunger and moving the needle over the surface of the balloon to be coated. Once all required coating solution is applied to the balloon, the balloon may be rotated for a short period of time to obtain a uniform distribution of coating solution over the coated surfaces and to allow the surface coating to partially dry.

Other needle deposition techniques may be used including one that meters small (e.g., nanoliter) droplets onto the surface of a balloon in a predefined pattern. The technology works by using piezoelectric pressure pulses to force liquid through a small, precision orifice to create tiny droplets that are expelled onto a surface. By controlling the magnitude of the pressure pulse, the size of a fluid droplet can be controlled very accurately. In this embodiment, coating solution fills a small chamber and an electrical signal is sent to a piezoelectric crystal, which generates a pressure pulse to inject tiny droplets onto the surface of a balloon. A nozzle is moved in a fixed pattern over the surface of the balloon to coat it uniformly with droplets. By placing small droplets in close proximity to one another, the uniformity of the coating from a clinical perspective is likely not compromised because the drug diffuses over short distances in a coronary artery. By having a pulse that injects the droplet onto the balloon, the need to provide precise containers for distribution of the coating solution may be eliminated. In addition, because the droplets are so small, complete drying of the coating generally occurs in minutes rather than hours.

EXAMPLES

XRD and Quantification of Crystalline/Amorphous Content of Drug

The coating was removed from the balloon surface using a spatula and the powder was placed on a silicon zero background sample holder and covered with a KAPTON film. The quantification of the crystalline and amorphous components was performed using Direct Derivation Quant Method (DDQM) available in the software package Highscore Plus (Panalytical, The Netherlands). The samples were subjected to the analyses by setting the instrumental parameters reported in the following table:

| Analytical technique | Abbreviation | Range | Other Info | Pre-treatment |
|---|---|---|---|---|
| X-Ray Powder Diffraction Rigaku Miniflex 600 | XRPD | 3-40°2Theta | Kapton film/zero-background | Powder removed from balloon surface by spatula. |

Example 1: Sirolimus with Urea (15:1 w/w)

Formulation Steps:
1. Sirolimus (SLMS) was dissolved in ethyl acetate (EA) approximately 110 milligrams per milliliter ($\approx$110 mg\mL) under stirring.
2. Methanol (Met) was added under stirring (EA\Met 9:1 volume\volume (v/v)).
3. Heptane (Hep) was added under stirring and very slowly ((EA−Met)/Hep 5:2 v/v).
4. Urea was dissolved in Met ($\approx$100 mg\mL).
5. A volume of urea solution equal to SLMS/Urea 15:1 weight\weight (wt/wt or w/w) was measured.
6. The SLMS solution was mixed with the urea solution.

Processing Steps for 6 mm×80 mm Balloon:
The coating solution described above was dispensed onto a balloon using an ADAPT Deposition Coater (Adapt Engineering Limited, Dublin, Ireland) and the following parameters:
Target Density: 7 µg\mm$^2$
Actual Density: 5.7 µg\mm$^2$
Balloon material and area: nylon 12 L25; area 16.6 cm$^2$
Volume dispensed: 171 µL (for each balloon SLMS: $\approx$11.6 mg; Urea: $\approx$0.77 mg)

| Passes | Wait Time (s) | Rotation (RPM) | Pass Speed (mm/s) | Syringe Volume (µL) | Fill Volume (µL) | Fill Rate (µL/s) | Dispense Rate (µL/s) |
|---|---|---|---|---|---|---|---|
| 72 | 2 | 17 | 60 | 250 | 171 | 25 | 2.5 |

Figure 3:
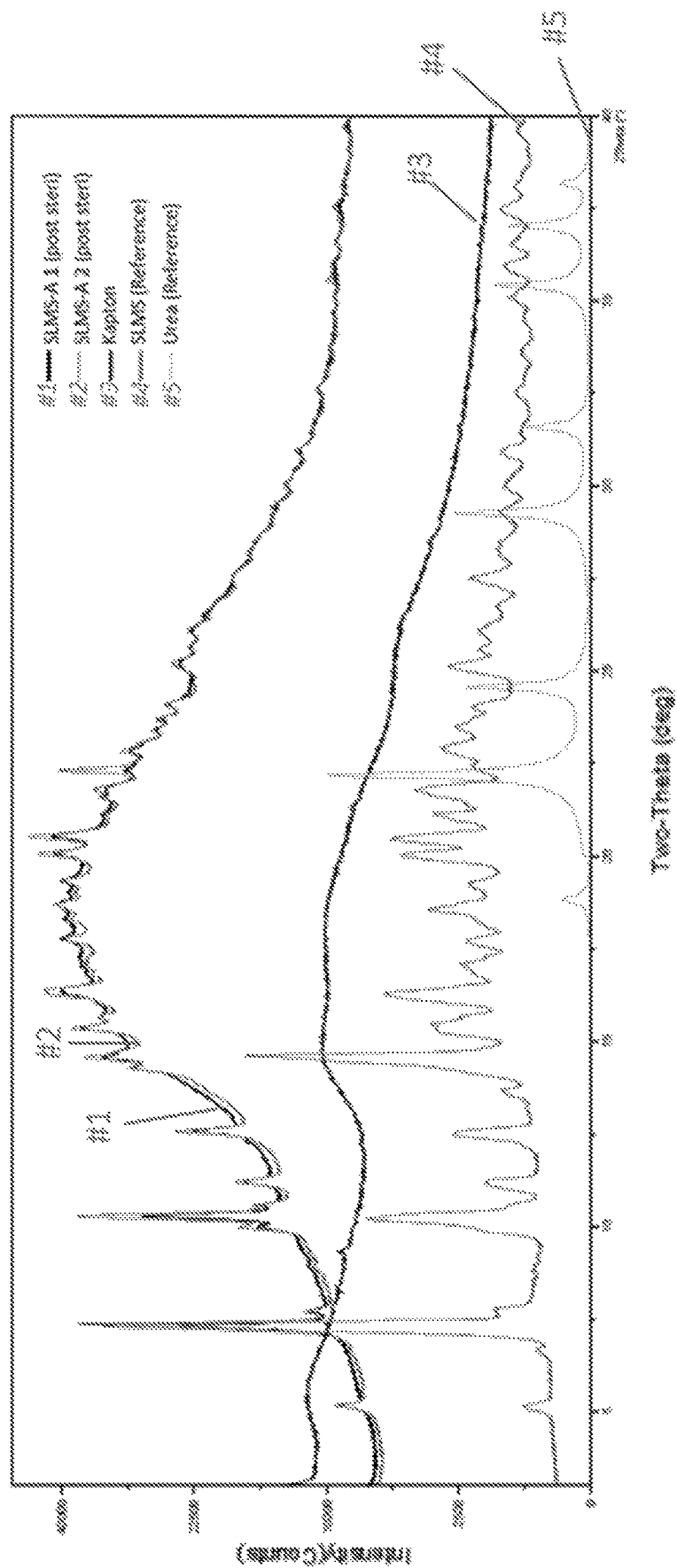
FIG. 3 is the X-ray diffraction of the coating of Example 1.

Coating Characterization:
The coating included 11% crystalline SLMS of the total amount of SLMS on the balloon.
X-ray diffraction of the coating is shown in FIG. 3. The top two lines (#1 and #2) are a comparison between the powder removed from two batches of Sirolimus with Urea (15:1 w/w) formulation after sterilization. Line #3 is an XRD of the KAPTON film. The bottom two lines are reference XRD patterns of crystalline SLMS (#4 line) and crystalline urea (#5 line) for comparison.

Scanning Electron Micrograph (SEM) showed surface cracking, minimal flaking, smooth surface features, and small pores and craters.

Example 2: Sirolimus with Urea (1000:1 w/w)

Formulation Steps:
1. Sirolimus (SLMS) was dissolved in ethyl acetate (EA) approximately 110 milligrams per milliliter ($\approx$110 mg\mL) under stirring.
2. Heptane (Hep) was added under stirring and very slowly (EA/Hep 5:3 v/v).
3. Urea was dissolved in Met ($\approx$100 mg\mL).
4. A volume of urea solution equal to SLMS/Urea 1000:1 weight\weight (wt/wt) was measured.
5. The SLMS solution was mixed with the urea solution.

Processing Steps for 6 mm×80 mm Balloon:
The coating solution described above was dispensed onto a balloon using an ADAPT Deposition Coater (Adapt Engineering Limited, Dublin, Ireland) and the following parameters:
Target Density: 7 μg\mm$^2$
Actual Density: 4.1 μg\mm$^2$
Balloon material and area: nylon 12 L25; area 16.6 cm$^2$
Volume dispensed: 158 μL (SLMS: $\approx$11.6 mg; Urea: $\approx$0.012 mg)

| Passes | Wait Time (s) | Rotation (RPM) | Pass Speed (mm/s) | Syringe Volume (μL) | Fill Volume (μL) | Fill Rate (μL/s) | Dispense Rate (μL/s) |
|---|---|---|---|---|---|---|---|
| 72 | 2 | 17 | 60 | 250 | 158 | 25 | 2.5 |

Figure 4:
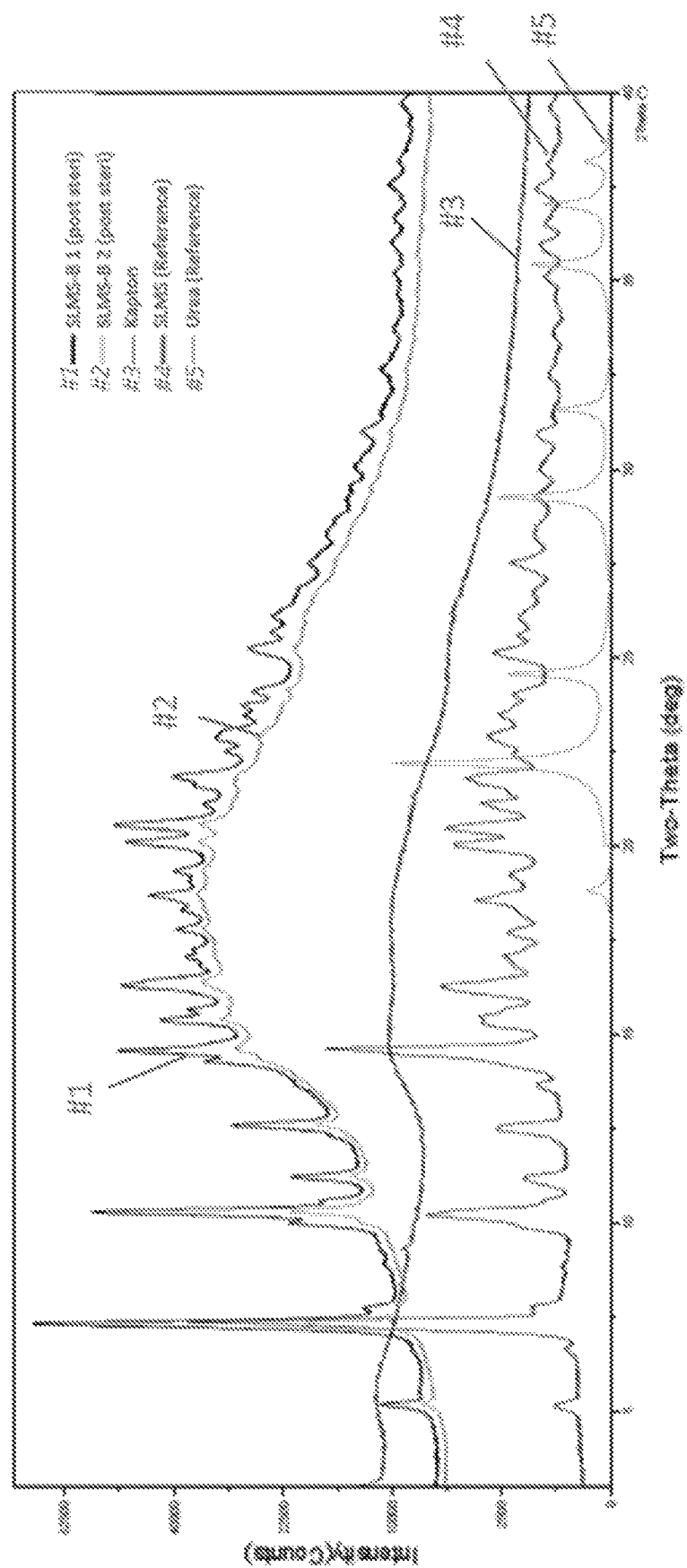
FIG. 4 is the X-ray diffraction of the coating of Example 2.

Coating Characterization:
The coating included 15% crystalline SLMS of the total amount of SLMS on the balloon.
X-ray diffraction of the coating is shown in FIG. 4. X-ray diffraction of the coating is shown in FIG. 4. The top two lines (#1 and #2) are a comparison between the powder removed from two batches of Sirolimus with Urea (1000:1 w/w) formulation after sterilization. Line #3 is an XRD of the KAPTON film. The bottom two lines are reference XRD patterns of crystalline SLMS (#4 line) and crystalline urea (#5 line) for comparison.
SEM showed deep coating cracking, significant flaking, rough surface with particulate, and small pores.

Example 3: Sirolimus (No Urea)

Formulation Steps:
1. Sirolimus (SLMS) was dissolved in ethyl acetate (EA) approximately 110 milligrams per milliliter 110 mg\mL) under stirring.
2. Heptane (Hep) was added under stirring and very slowly (EA/Hep 5:3 v/v).

Processing Steps for 6 mm×80 mm Balloon:
The coating solution described above was dispensed onto a balloon using an ADAPT Deposition Coater (Adapt Engineering Limited, Dublin, Ireland) and the following parameters:
Target Density: 7 μg\mm$^2$
Actual Density: 5.5 μg\mm$^2$
Balloon material and area: nylon 12 L25; area 16.6 cm$^2$
Volume dispensed: 158 μL (SLMS: $\approx$11.6 mg)

| Passes | Wait Time (s) | Rotation (RPM) | Pass Speed (mm/s) | Syringe Volume (μL) | Fill Volume (μL) | Fill Rate (μL/s) | Dispense Rate (μL/s) |
|---|---|---|---|---|---|---|---|
| 72 | 2 | 17 | 60 | 250 | 158 | 25 | 2.5 |

Coating Characterization:
The amount of crystalline SLMS on the balloon was not determined.
SEM showed a significant amount of surface cracking, rough surface with particulate, small pores, and minimal craters.

Example 4: Zotarolimus with Urea (150:1 w/w)

Formulation Steps:
1. Urea was dissolved in Acetone (ACT) ($\approx$3 mg\mL).
2. Zotaroliums (ZLMS) was dissolved in ACT\urea solution ($\approx$470 mg\mL) (ZLMS\urea 150:1 wt\wt.) under stirring.
3. Hexane (Hex) was added under stirring and very slowly (ACT\Hex 1:1.5 v\v).

Processing Steps for 6 mm×80 mm Balloon:
The coating solution described above was dispensed onto a balloon using an ADAPT Deposition Coater (Adapt Engineering Limited, Dublin, Ireland) and the following parameters:
Target Density: 7 μg\mm$^2$
Actual Density: 6.0 μg\mm$^2$
Balloon material and area: nylon 12 L25; area 16.6 cm$^2$
Volume dispensed: 62 μL (ZLMS: 11.6 mg; Urea: $\approx$0.078 mg)

| Passes | Wait Time (s) | Rotation (RPM) | Pass Speed (mm/s) | Syringe Volume (μL) | Fill Volume (μL) | Fill Rate (μL/s) | Dispense Rate (μL/s) |
|---|---|---|---|---|---|---|---|
| 50 | 2 | 17 | 60 | 250 | 62 | 25 | 2.5 |

Coating Characterization:
The coating included 0% crystalline ZLMS of the total amount of ZLMS on the balloon.
SEM showed minimal flaking and cracking, smooth surface, significant pores of all sizes, and significant craters.

Pharmokinetic Test Results
External and internal femoral arteries of pigs were used to assess the in-vivo transfer of the drug coating to an arterial vessel. A dissection was made to the common carotid artery, and an intravascular ultrasound (IVUS) catheter was inserted into the artery and directed under fluoroscopic guidance to the treatment site of the femoral artery. Contrast agent was injected through the catheter and angiograms of the femoral arteries recorded. A pull back of IVUS was recorded for optimal balloon to artery ratio inflations (1.05-1.41).

The IVUS catheter was exchanged for a 6 mm diameter× 80 mm length drug coated angioplasty balloon catheter under fluoroscopic guidance and inflated at the target treatment artery for 180 seconds. The balloon was deflated and withdrawn. Both the right and left external and internal femoral arteries of each animal were treated.

A total of twelve arteries were treated with each drug coated angioplasty balloon catheter design, six arteries were recovered at each time point of 1 day and 28 days. The vessel segments were recovered and assayed for drug content by HPLC quantification. Assay of the treated vessel segments demonstrated tissue drug levels shown in the following table.

| Pharmacokinetic Results | | |
|---|---|---|
| Example | t = 1 day Avg pK (µg/g) | t = 28 day Avg pK (µg/g) |
| Example 1: SLMS with Urea (15:1 w/w) | 5.32 (n = 6) | 3.77 (n = 6) |
| Example 2: SLMS with Urea (1000:1 w/w) | 1.93 (n = 6) | 0.17 (n = 6) |
| Example 4: ZLMS with Urea (150:1 w/w) | 5.20 (n = 6) | 1.54 (n = 6) |

The complete disclosures of the patents, patent documents, and publications cited herein are incorporated by reference in their entirety as if each were individually incorporated. To the extent that there is any conflict or discrepancy between this specification as written and the disclosure in any document that is incorporated by reference herein, this specification as written will control. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. An angioplasty balloon comprising a surface having disposed thereon a single-layer coating comprising at least one limus drug, a portion of which is in the form of crystals, wherein no more than 30 wt-% of the total limus drug is in the form of crystals, and further wherein the angioplasty balloon is in a deployable configuration.

2. The angioplasty balloon of claim 1 wherein 1 wt-% to 25 wt-% of the total limus drug is in the form of crystals.

3. The angioplasty balloon of claim 1 wherein the limus drug comprises sirolimus.

4. The angioplasty balloon of claim 1 wherein the single-layer coating further comprises at least one excipient.

5. The angioplasty balloon of claim 4 wherein the excipient is a nonpolymeric compound.

6. The angioplasty balloon of claim 5 wherein the excipient comprises urea.

7. The angioplasty balloon of claim 4 wherein the excipient is present in the single-layer coating in a limus drug to excipient ratio of greater than 20:1.

8. An angioplasty balloon comprising a surface having disposed thereon a single-layer coating comprising at least one nonpolymeric excipient and at least one limus drug, wherein the excipient is present in the single-layer coating in a limus drug to excipient ratio of greater than 20:1, and further wherein the angioplasty balloon is in a deployable configuration.

9. The angioplasty balloon of claim 8 wherein the limus drug comprises sirolimus, zotarolimus, or combinations thereof.

10. The angioplasty balloon of claim 8 wherein the nonpolymeric excipient comprises urea.

11. The angioplasty balloon of claim 8 wherein the single-layer coating is polymer free.

12. A method of coating an angioplasty balloon, the method comprising:
  forming a coating solution comprising at least one limus drug and a mixture of organic solvents, at least two of which have different rates of evaporation;
  applying the coating solution to a surface of an angioplasty balloon in one step using needle deposition; and
  allowing the mixture of solvents to evaporate and form a single-layer coating comprising at least one limus drug.

13. The method of claim 12 wherein the single-layer coating comprises at least one limus drug, at least a portion of which is in crystalline form.

14. The method of claim 12 wherein the mixture of solvents comprises at least one apolar solvent and at least one polar solvent, wherein the ratio of apolar solvent to polar solvent is in a range of 35:65 to 45:55.

15. The method of claim 14 wherein the apolar solvent comprises heptane, hexane, or a combination thereof and the polar solvent comprises ethyl acetate, methanol, ethanol, isopropyl alcohol, acetone, or combinations thereof.

16. The method of claim 15 wherein the mixture of solvents comprises ethyl acetate and heptane.

17. The method of claim 15 wherein the mixture of solvents comprises acetone and hexane.

18. The method of claim 12 wherein the concentration of limus drug in the coating solution is in a range of 95 wt-% to 99.9 wt-%, based on the total weight of the solute in the coating solution.

19. The method of claim 12 wherein the solution further comprises at least one excipient.

20. The method of claim 19 wherein the concentration of excipient in the coating solution is in a range of 0.1 wt-% to 5 wt-%, based on the total weight of the solute in the coating solution.

* * * * *